United States Patent [19]

Yoshioka et al.

[11] Patent Number: 5,169,946
[45] Date of Patent: Dec. 8, 1992

[54] PROCESS FOR PREPARING 1,5-BENZOTHIAZEPINE DERIVATIVE

[75] Inventors: Masanori Yoshioka, Chiba; Mitsuyoshi Wagatsuma, Urawa; Akiyoshi Yoda, Tokyo; Yoshihisa Yamada; Gunji Yoshimura, both of Onoda, all of Japan

[73] Assignee: Tanabe Seiyaku Co., Ltd., Osaka, Japan

[21] Appl. No.: 805,561

[22] Filed: Nov. 27, 1991

[30] Foreign Application Priority Data

Nov. 29, 1990 [JP] Japan ................... 2-336010

[51] Int. Cl.$^5$ .................. A61K 31/55; C07D 281/10
[52] U.S. Cl. ................................................ 540/491
[58] Field of Search ......................................... 540/491

[56] References Cited

U.S. PATENT DOCUMENTS 3,562,257  2/1971  Kugita et al. ............... 540/491
4,590,188  5/1986  Takeda et al. .............. 540/491

FOREIGN PATENT DOCUMENTS 47-813    1/1972  Japan ...................... 540/491
53-18038  6/1978  Japan ...................... 540/491
62-132876 6/1987  Japan ...................... 540/491

OTHER PUBLICATIONS

Chemical Abstracts, vol. 107, No. 21, Nov. 23, 1987, Columbus, Ohio, U.S.; abstract No. 198367U, p. 770; abstract.

"Brief Comments on Relevant Arts", which contains comments concerning each of the above listed Japanese Patent Publications 813/1972, 18038/1978, and 132876/1987.

Primary Examiner—Robert T. Bond
Attorney, Agent, or Firm—Browdy and Neimark

[57] ABSTRACT

A process for preparing hydrochloride of 3-acetoxy-2,3-dihydro-5-[2-(dimethylamino)ethyl]-2-(p-methoxyphenyl)-1,5-benzothiazepin-4(5H)-one which comprises reacting 3-hydroxy-2,3-dihydro-5-[2-(dimethylamino)ethyl]-2-(p-methoxyphenyl)-1,5-benzothiazepin-4(5H)-one which acetyl chloride in acetic acid or a mixed solvent of acetic acid and acetic anhydride. According to the process, hydrochloride of 3-acetoxy-2,3-dihydro-5-[2-(dimethylamino)ethyl]-2-(p-methoxyphenyl)-1,5-benzothiazepin-4(5H)-one is readily obtained in one step.

7 Claims, No Drawings

_5,169,946_

PROCESS FOR PREPARING 1,5-BENZOTHIAZEPINE DERIVATIVE

BACKGROUND OF THE INVENTION

The present invention relates to a process for preparing hydrochloride of 3-acetoxy-2,3-dihydro-5-[2-(dimethylamino)ethyl]-2-(p-methoxyphenyl)-1,5-benzothiazepin-4(5H)-one which is useful as a medicinal compound.

Hydrochloride of 3-acetoxy-2,3-dihydro-5-[2-(dimethylamino)ethyl]-2-(p-methoxyphenyl)-1,5-benzothiazepin-4(5H)-one (hereinafter referred to as desired compound), particularly, d-cis form thereof is a medicinal compound useful as a coronary vasodilator and an anti-hypertensive agent. Hitherto, there have been known some processes for preparing the desired compound. Examples of these processes are, for instance, (1) a process wherein 3-hydroxy-2,3-dihydro-5-[2-(dimethylamino)ethyl]-2-(p-methoxyphenyl)-1,5-benzothiazepin-4(5H)-one (hereinafter referred to as 3-hydroxy compound) is reacted with an acetylating agent such as acetic anhydride with heating to give 3-acetoxy-2,3-dihydro-5-[2-(dimethylamino)ethyl]-2-(p-methoxyphenyl)-1,5-benzothiazepin-4(5H)-one (hereinafter referred to 3-acetoxy compound) according to a conventional method and then the resulting 3-acetoxy compound is treated with ethanolic hydrogen chloride (or methanolic hydrogen chloride) (see Japanese Examined Patent Publication No. 813/1972 and No. 18038/1978), (2) a process wherein the 3-hydroxy compound is reacted with acetic anhydride in the presence of hydrochloric acid in one step (see Japanese Unexamined Patent Publication No. 132876/1987) and the like.

However, in the process (1), two steps, namely, a step for the acetylation and a step for the formation of hydrochloride, are required to be carried out separately, although the acetylation can be suitably carried out in the absence of water. On the other hand, in the process (2), hydrochloric acid must be at first added with cooling and then the acetylation is carried out with heating, since heat is generated on the addition of hydrochloric acid (aqueous solution of hydrogen chloride) used as a supplier of hydrogen chloride. The operations in the method (2) are, therefore, complicated. Further, it is always required in the method (2) to use a large exess of acetic anhydride for removing water existing in the reaction system, which is introduced on the addition of hydrochloric acid, since the acetylation cannot be completed in the presence of water.

An object of the invention is to provide a process for simply preparing the desired compound from the 3-hydroxy compound in one step without cooling the reaction system or using a large excess of an acetylating agent.

This and the other objects of the present invention will become apparent from the description hereinafter.

SUMMARY OF THE INVENTION

It has now been found that a process for preparing hydrochloride of 3-acetoxy-2,3-dihydro-5-[2-(dimethylamino)ethyl]-2-(p-methoxyphenyl)-1,5-benzothiazepin-4(5H)-one which comprises reacting 3-hydroxy-2,3-dihydro-5-[2-(dimethylamino)ethyl]-2-(p-methoxyphenyl)-1,5-benzothiazepin-4(5H)-one with acetyl chloride in acetic acid or a mixed solvent of acetic acid and acetic anhydride overcomes the defects of the above-mentioned conventional processes.

DETAILED DESCRIPTION

The above-mentioned process of the present invention is established based upon a novel knowledge that acetyl chloride acts as not only an acetylating agent for the 3-hydroxy compound but also a supplier of hydrogen chloride, resulting in giving the desired compound. According to the process of the present invention, therefore, the desired compound can be prepared quantitatively without supplying hydrogen chloride separately, using a large excess of an acetylating agent or cooling the reaction system which are needed in conventional processes.

In the process of the present invention, acetic acid or a mixed solvent of acetic acid and acetic anhydride can be suitably used as a solvent. As to the mixing ratio of the mixed solvent, the amount of acetic anhydride may be about one-tenth of the amount of acetic acid or may be increased to several times of the amount of acetic acid. The mixing ratio of the mixed solvent can be appropriately selected according to the reaction temperature or a desired reaction time. The amount of the solvent to be used is not particularly limited and, for example, the amount is sufficiently from about 1 to about 5 parts by weight per part by weight of the 3-hydroxy compound. Suitable amount of acetyl chloride to be used may vary according to the solvent, but are usually within 1 to 20 moles per mole of the 3-hydroxy compound. For example, when only acetic acid is used as the solvent, it is preferred to use acetyl chloride in an amount of more than 1 mole, preferably 1.01 to 10 moles, more preferably 1.05 to 1.5 moles, per mole of the 3-hydroxy compound. On the other hand, when a mixture of acetic acid and acetic anhydride is used as the solvent, it is preferred to use acetyl chloride in an amount of not less than 1 mole, preferably 1 to 5 moles, more preferably 1 to 1.5 moles, per mole of the 3-hydroxy compound.

The process of the present invention can be carried out at from a low temperature with cooling, for instance 5° C., to a high temperature with heating, for instance 130° C., preferably from the room temperature to a refluxing temperature. Especially, when only acetic acid is used as the solvent, it is preferred to carry out the process at 10° to 110° C., more preferably 40° to 80° C. On the other hand, when a mixture of acetic acid and acetic anhydride is used as the solvent, it is preferred to carry out the process at 5° to 130° C., more preferably 10° to 110° C.

In case that a mixed solvent of acetic acid and acetic anhydride is used in the present invention, the reaction is accelerated and the solvent is prevented from freezing when temperature lowering.

With respect to the 3-hydroxy compound which is the starting material of the present invention, there are four stereoisomers owing to asymmetric carbon atoms at the 2-position and the 3-position. Since the process of the present invention can be carried out without racemization, the desired compound having an optical activity can be obtained from the 3-hydroxy compound having the corresponding optical activity.

Isolation of the desired compound after the completion of the reaction can be easily carried out according to the conventional methods such as recrystallization after distilling the reaction solvent away.

As indicated in the following Examples, according to the process of the present invention, the desired compound can be obtained in a high yield in one step without carrying out another step to obtain the hydrochloride after the acetylation or adding hydrochloric acid to a reaction system, since acethyl chloride acts as not only an acetylating agent but also a supplier of hydrogen chloride.

The process of the present invention, therefore, has an industrially excellent advantage that the desired compound can be obtained by a simple operation in a high yield, compared with other conventional methods. For example, while two steps, namely a step for the acetylation and a step for the formation of the hydrochloride, are required to be carried out separately in the process (1) described in Japanese Examined Patent Publication No. 813/1972 and No. 13038/1978, the desired compound can be obtained in one step in the present invention. Further, while a large excess of acetic anhydride is required to be used in order to remove water existing in the reaction system, which is intruduced on the addition of hydrochloric acid (aqueous solution of hydrogen chloride), from the reaction system in the process (2) described in Japanese Unexamined Patent Publication No. 132876/1987, only 1 mole or a little more than 1 mole of acetyl chloride per mole of the 3-hydroxy compound may be sufficiently used in the present invention, which does not require the addition of hydrochloric acid with cooling, to obtain the desired compound in a high yield.

The present invention is more specifically described and explained by means of the following Experimental Examples and Examples. It is to be understood that the present invention is not limited to the Examples, and various changes and modifications may be made in the invention without departing from the spirit and scope thereof.

EXPERIMENTAL EXAMPLE 1

Effect of a Solvent for the Acetylation on Conversion Rate

In 200 ml of each solvent described in Table 1 were mixed 25 g of the d-cis-3-hydroxy compound and 5.8 g of acetyl chloride (1.1 moles per mole of the d-cis-3-hydroxy compound) and each mixture was stirred at 30° C. for 2 hours. Conversion rate to the desired compound was determined by high performance liquid chromatography. The results are shown in the following Table 1. When acetic acid or a mixed solvent of acetic acid and acetic anhydride was used, the desired compound was obtained in a significantly high conversion rate compared with those in case of using other solvents.

TABLE 1

| | Solvent | Conversion rate to the desired compound |
|---|---|---|
| Solvents used in the present invention | Acetic acid | 95% |
| | Mixed solvent A | 99.98% *2) |
| | Mixed solvent B | 100% *2) |
| Other solvents (Reference) | Acetic anhydride | 33% *2) |
| | Chloroform | 78% |
| | Methylene chloride | 70% |
| | Dichloroethane | 77% |
| | Acetone | 51% |
| | Trichloroethane | 66% |

TABLE 1-continued

| Solvent | Conversion rate to the desired compound |
|---|---|
| Toluene | 78% |

Mixed solvent A: acetic acid: acetic anhydride = 1:1
Mixed solvent B: acetice acid: acetic anhydride = 1:3
*2) The used amount of acetyl chloride was 1.2 moles per mole of the d-cis-3-hydroxy compound and the reaction system was stirred at 60° C. for 3 hours.

EXAMPLE 1

In 15 ml of acetic acid was dissolved 7.45 g (0.02 mole) of d-cis-3-hydroxy-2,3-dihydro-5-[2-(dimethylamino)ethyl]-2-(p-methoxyphenyl)-1,5-benzothiazepin-4(5H)-one with heating. Then thereto was added 1.71 g (0.022 mole) of acetyl chloride at 20° C. and the mixture was stirred at room temperature for 72 hours. After the reaction, acetic acid was distilled away and the residue was recrystallized from ethanol to give 7.53 g of hydrochloride of d-cis-3-acetoxy-2,3-dihydro-5-[2-(dimethylamino)ethyl]-2-(p-methoxyphenyl)-1,5-benzothiazepin-4(5H)-one.

yield: 83%.
m.p.: 213°–214° C.

EXAMPLE 2

The procedure of Example 1 was repeated except that the reaction was carried out at 70°–80° C. for 3 hours with stirring and 97% ethanol was used for the recrystallization to give 8.45 g of hydrochloride of the d-cis-3-acetoxy compound.

yield: 94%.

Physical properties of the obtained compound coincided with those of the desired compound in Example 1.

EXAMPLE 3

The procedure of Example 1 was repeated except for the followings. As reactants, 50 g (0.13 mole) of d-cis-3-hydroxy-2,3-dihydro-5-[2-(dimethylamino)ethyl]-2-(p-methoxyphenyl)-1,5-benzothiazepin-4(5H)-one and 12.7 g (0.16 mole) of acetyl chloride were used. The reaction was carried out at 60° C. for 3 hours with stirring in a mixed solvent of 81 ml of acetic acid and 19 ml of acetic anhydride and 97% ethanol was used for the recrystallization. Thus 55.9 g of the hydrochloride of the d-cis-3-acetoxy compound was obtained.

yield: 92%.

Physical properties of the obtained compound coincided with those of the desired compound in Example 1.

EXAMPLE 4

The procedure of Example 1 was repeated except for the followings. As reactants, 50 g (0.13 mole) of d-cis-3-hydroxy-2,3-dihydro-5-[2-(dimethylamino)ethyl]-2-(p-methoxyphenyl)-1,5-benzothiazepin-4(5H)-one and 10.8 g (0.13 mole) of acetyl chloride were used. The reaction was carried out at 100°–110° C. for 6 hours with stirring in a mixed solvent of 50 ml of acetic acid and 50 ml of acetic anhydride and 97% ethanol was used for the recrystallization. Thus 53.7 g of the hydrochloride of the d-cis-3-acetoxy compound was obtained.

yield: 89%.

Physical properties of the obtained compound coincided with those of the desired compound in Example 1.

EXAMPLE 5

The procedure of Example 1 was repeated except for followings. As reactants, 50 g (0.13 mole) of d-cis-3- hydroxy-2,3-dihydro-5-[2-(dimethylamino)ethyl]-2-(p-methoxyphenyl)-1,5-benzothiazepin-4(5H)-one and 12.7 g (0.16 mole) of acethyl chloride were used. The reaction was carried out at 60° C. for 3 hours with stirring in a mixed solvent of 25 ml of acetic acid and 75 ml of acetic anhydride and 97% ethanol was used for the recrystallization. Thus 54.7 g of the hydrochloride of the d-cis-3-acetoxy compound was obtained.

yield: 90.4%.

Physical properties of the obtained compound coincided with those of the desired compound in Example 1.

What we claim is:

1. A process for preparing 3-acetoxy-2,3-dihydro-5-[2-(dimethylamino)ethyl]-2-(p-methoxyphenyl)-1,5-benzothiazepine-4(5H)-one hydrochloride which comprises reacting free 3-hydroxy-2,3-dihydro-5-[2-(dimethylamino)ethyl]-2-(p-methoxyphenyl)-1,5-benzothiazepin-4(5H)-one with acetyl chloride in acetic acid or acetyl chloride in a mixed solvent of acetic acid and acetic anhydride.

2. The process of claim 1, wherein 1 to 20 moles of acetyl chloride is used per mole of a 3-hydroxy-1,5-benzothiazepine derivative which is a starting material.

3. The process of claim 1, wherein the reaction is carried out in acetic acid by using 1.01 to 10 moles of acetyl chloride per mole of a 3-hydroxy-1,5-benzothiazepine derivative which is a starting material.

4. The process of claim 1, wherein the reaction is carried out in a mixed solvent of acetic acid and acetic anhydride by using 1 to 5 moles of acetyl chloride per mole of a 3-hydroxy-1,5-benzothiazepine derivative which is a starting material.

5. The process of claim 1, wherein a d-cis form of a 3-hydroxy-1,5-benzothiazepine derivative is used as a starting material.

6. The process of claim 1, wherein the 3-acetoxy-2,3-dihydro-5-[2-(dimethylamino)ethyl]-2-(p-methoxyphenyl)-1,5-benzothiazepine-4(5H)-one hydrochloride produced obtains the chloride from the acetyl chloride.

7. A process for preparing 3-acetoxy-2,3-dihydro-5-[2-(dimethylamino)ethyl]-2-(p-methoxyphenyl)-1,5-benzothiazepine-4(5H)-one hydrochloride from free 3-hydroxy-2,3-dihydro-5-[2-(dimethylamino)ethyl]-2-(p-methoxyphenyl)-1,5-benzothiazepine-4(5H)-one in a single step, comprising reacting said free 3-hydroxy-2,3-dihydro-5-[2-(dimethylamino)ethyl]-2-(p-methoxyphenyl)-1,5-benzothiazepine-4(5H)-one with acetyl chloride in a solvent of acetic acid or a mixture of acetic acid and acetic anhydride.

* * * * *